(12) United States Patent
Mustafa et al.

US012419857B2

(10) Patent No.: US 12,419,857 B2
(45) Date of Patent: Sep. 23, 2025

(54) ORAL TOPIRAMATE SUSPENSION FORMULATIONS WITH EXTENDED SHELF STABILITY AND ENHANCED BIOAVAILABILITY

(71) Applicant: Rosemont Pharmaceuticals Limited, Leeds (GB)

(72) Inventors: Tajamal Mustafa, Leeds (GB); Mark Kneale Foley, Leeds (GB); Hayley Louise Lonergan, Leeds (GB); David Robert Thompson, Leeds (GB)

(73) Assignee: Rosemont Pharmaceuticals Limited, Leeds (GB)

( * ) Notice: Subject to any disclaimer, the term of this patent is extended or adjusted under 35 U.S.C. 154(b) by 968 days.

(21) Appl. No.: 17/295,933

(22) PCT Filed: Nov. 21, 2018

(86) PCT No.: PCT/IB2018/059194
§ 371 (c)(1),
(2) Date: May 21, 2021

(87) PCT Pub. No.: WO2020/104837
PCT Pub. Date: May 28, 2020

(65) Prior Publication Data
US 2022/0016074 A1   Jan. 20, 2022

(51) Int. Cl.
| | | |
|---|---|---|
| *A61K 31/36* | (2006.01) |
| *A61K 9/00* | (2006.01) |
| *A61K 47/02* | (2006.01) |
| *A61K 47/10* | (2017.01) |
| *A61K 47/12* | (2006.01) |
| *A61K 47/26* | (2006.01) |
| *A61K 47/34* | (2017.01) |
| *A61K 47/36* | (2006.01) |

(52) U.S. Cl.
CPC ............ *A61K 31/36* (2013.01); *A61K 9/0053* (2013.01); *A61K 47/02* (2013.01); *A61K 47/10* (2013.01); *A61K 47/12* (2013.01); *A61K 47/26* (2013.01); *A61K 47/34* (2013.01); *A61K 47/36* (2013.01)

(58) Field of Classification Search
CPC ...... A61K 31/36; A61K 9/0053; A61K 47/02; A61K 47/10; A61K 47/12; A61K 47/26; A61K 47/34; A61K 47/36
See application file for complete search history.

(56) References Cited

U.S. PATENT DOCUMENTS

| | | | |
|---|---|---|---|
| 9,492,380 B2 * | 11/2016 | Jacob | .................. A61K 9/2018 |
| 2008/0260813 A1 | 10/2008 | Thakur | |
| 2015/0024055 A1 | 1/2015 | Liang | |
| 2016/0235776 A1 | 8/2016 | Kulkarni | |

FOREIGN PATENT DOCUMENTS

CN    106109408 A    11/2016

OTHER PUBLICATIONS

Allen, Loyd V. "Topiramate 20 mg/mL oral suspension." US Pharm 42.5 (2017): 46-7. (Year: 2017).*
International Search Report from Appl. No. PCT/IB2018/059194, mailed on Jan. 8, 2019.
Ora-Plus, Perrigo, NDC #0574-0303-16, p. 1-2, (2014).
Ora-Sweet, Perrigo, (2019), p. 1-2.

\* cited by examiner

*Primary Examiner* — Joseph K McKane
*Assistant Examiner* — Quincy McKoy
(74) *Attorney, Agent, or Firm* — Nevrivy Patent Law Group P.L.L.C.

(57) ABSTRACT

The present application relates to pharmaceutical compositions comprising a pharmaceutically effective amount of topiramate particles dispersed in suspension, wherein the composition is suitable for oral delivery. The present application also relates to cold-chain stable formulations of oral liquid suspension dosage forms containing topiramate and a process for producing the oral liquid suspension dosage forms.

5 Claims, 7 Drawing Sheets

Topiramate PCT Application FIGURES
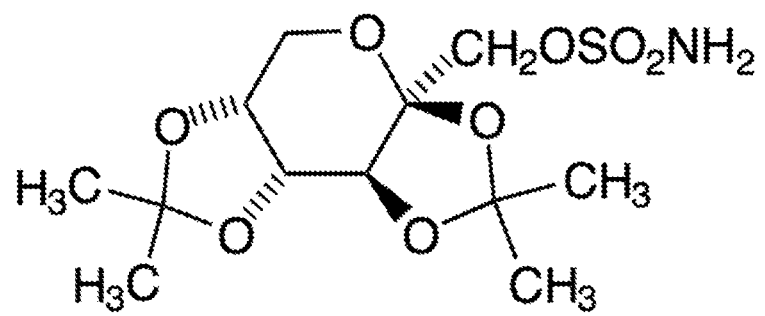
Fig. 1 Chemical structure of topiramate

| Excipient | Specification | Concentration (%w/v) | | Use |
|---|---|---|---|---|
| | | 10mg/ml | 20mg/ml | |
| Citric Acid Monohydrate | Ph. Eur | 0.14 | 0.14 | Acidic adjunct to pH Buffer |
| Disodium Hydrogen Phosphate Dihydrate | Ph. Eur | 1.6 | 1.6 | Basic adjunct to pH buffer |
| Simethicone | USP | 0.05 | 0.05 | Anti-Foam Agent |
| Sucralose E955 | Ph. Eur | 0.2 | 0.2 | Sweetener |
| Blackcurrant Flavor | HSE | 0.3 | 0.3 | Flavoring agent |
| Topiramate | HSE | 1.0 | 2.0 | Drug Substance |
| Sodium Methyl Hydroxybenzoate | Ph. Eur | 0.13 | 0.13 | Antimicrobial Preservative |
| Sodium Ethyl Hydroxybenzoate | Ph. Eur | 0.07 | 0.07 | |
| Dilute Hydrochloric acid | Ph. Eur | 0.132 | 0.132 | Adjunct to pH buffer |
| Xanthan Gum | Ph. Eur | 0.5 | 0.5 | Suspending Agent |
| Glycerol | Ph. Eur | 40.0 | 40.0 | Bulk vehicle / sweetener |
| Purified Water | HSE | To 100 | To 100 | Bulk Vehicle |

Fig. 2 Topiramate suspension compositions

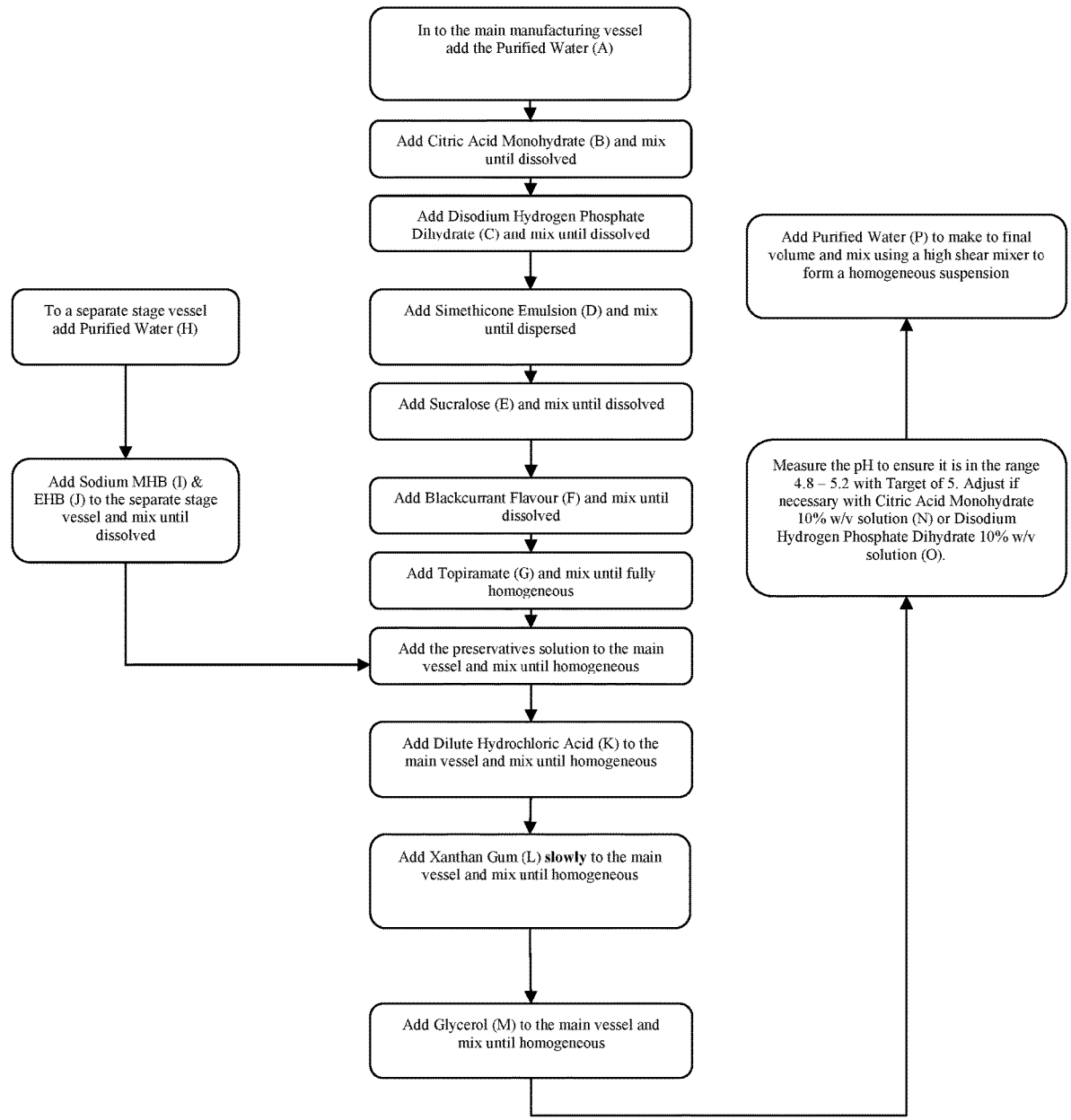
Fig. 3 Manufacture of topiramate suspension compositions

| Drug Substance | Topiramate | |
|---|---|---|
| Drug Substance Manufacturer Lot No. | Drug Substance Lot No. | PSD |
| A | 1 | D(10) 1.6μm<br>D(90) 7.2μm |
| B | 2 | D(10) 1.8μm<br>D(90) 12.2μm |
| C | 3 | D(10) 1.6μm<br>D(90) 10.4μm |

Fig. 4 Particle size distribution of topiramate suspension starting API.

| Lot no. (bulk lot no.) | Strength mg/ml | wt/mL (g) | Viscosity (cP) | Particle size | | | Dissolution; pH 4.5 45 min |
|---|---|---|---|---|---|---|---|
| | | | | D(V,0.1) | D(V,0.5) | D(V,0.9) | % dose |
| | | | | (µm) | | | |
| A | 10 | 1.107 | 1475 | 3.912 | 10.072 | 28.574 | 92.48 |
| B | 10 | 1.107 | 1468 | 4.681 | 10.946 | 24.781 | 91.35 |
| C | 10 | 1.107 | 1482 | 7.940 | 18.103 | 36.236 | 93.12 |
| D | 10 | 1.107 | 1490 | 8.204 | 17.362 | 35.009 | 94.53 |
| E | 20 | 1.110 | 1570 | 6.213 | 14.064 | 28.828 | 88.17 |
| F | 20 | 1.109 | 1562 | 8.073 | 16.168 | 30.750 | 88.83 |
| G | 20 | 1.108 | 1587 | 7.491 | 15.475 | 28.238 | 98.85 |
| H | 20 | 1.108 | 1566 | 7.994 | 16.185 | 29.123 | 96.20 |
| I | 10 | 1.105 | 1468 | 6.372 | 14.962 | 29.569 | 97.14 |
| J | 10 | 1.104 | 1516 | 6.400 | 15.123 | 30.267 | 95.16 |
| K | 20 | 1.112 | 1568 | 7.055 | 14.678 | 26.922 | 96.55 |
| L | 20 | 1.111 | 1575 | 7.171 | 15.127 | 27.868 | 92.60 |
| [1]M | 10 | 1.127 | 1575 | 4.344 | 12.510 | 32.274 | 86.31 |
| [2]N | 10 | 1.085 | 1450 | 3.064 | 8.593 | 20.919 | 98.62 |
| [3]O | 10 | 1.106 | 2000 | 3.007 | 8.604 | 21.509 | 76.44 |
| [4]P | 10 | 1.106 | 1175 | 3.527 | 10.919 | 27.015 | 98.52 |
| [1]Q | 20 | 1.131 | 1745 | 6.469 | 15.576 | 33.050 | 82.20 |
| [2]R | 20 | 1.087 | 1515 | 7.686 | 16.700 | 33.179 | 99.60 |
| [3]S | 20 | 1.107 | 2155 | 3.639 | 11.330 | 26.877 | 85.68 |
| [4]T | 20 | 1.107 | 1177 | 5.313 | 15.930 | 34.359 | 101.96 |

Key:  [1]High Glycerol
 [2]Low Glycerol
 [3]High Xanthan
 [4]Low Xanthan

Fig. 5 Viscosity, particle size and dissolution parameters of topiramate suspensions.

| Excipient | WHO maximum daily intake (mg/Kg/day) | Maximum daily intake allowed for 70 Kg Adult (mg) | Amount supplied per ml of product (mg) | Amount supplied by maximum daily intake of product (mg) 10mg/ml (50ml) | Amount supplied by maximum daily intake of product (mg) 20mg/ml (25ml) |
|---|---|---|---|---|---|
| Sucralose | 15.0 mg | 1050 mg | 2.0 mg | 100.0 mg | 50.0 mg |
| Simethicone | 1.5 mg | 105 mg | 0.5 mg | 25.0 mg | 12.5 mg |
| Methyl Hydroxybenzoate | 10.0 mg | 700.0 mg | 1.32 mg | 66.0 mg | 33.0 mg |
| Ethyl Hydroxybenzoate | 10.0 mg | 700.0 mg | 0.66 mg | 33.0 mg | 16.5 mg |

| Excipient | WHO maximum daily intake (mg/Kg/day) | Maximum daily intake allowed for 60 Kg child (mg) | Amount supplied per ml of product (mg) | Amount supplied by maximum daily intake of product (mg) 10mg/ml (40ml) | Amount supplied by maximum daily intake of product (mg) 20mg/ml (20ml) |
|---|---|---|---|---|---|
| Sucralose | 15.0 mg | 900.0 mg | 2.0 mg | 80.0 mg | 40.0 mg |
| Simethicone | 1.5 mg | 90.0 mg | 0.5 mg | 20.0 mg | 10.0 mg |
| Methyl Hydroxybenzoate | 10.0 mg | 600.0 mg | 1.32 mg | 52.8 mg | 26.4 mg |
| Ethyl Hydroxybenzoate | 10.0 mg | 600.0 mg | 0.66 mg | 26.4 mg | 13.2 mg |

| Excipient | WHO maximum daily intake (mg/Kg/day) | Maximum daily intake allowed for 12 Kg child (mg) | Amount supplied per ml of product (mg) | Amount supplied by maximum daily intake of product (mg) 10mg/ml (10ml) | Amount supplied by maximum daily intake of product (mg) 20mg/ml (5ml) |
|---|---|---|---|---|---|
| Sucralose | 15.0 mg | 180.0 mg | 2.0 mg | 20.0 mg | 10.0 mg |
| Simethicone | 1.5 mg | 18.0 mg | 0.5 mg | 5.0 mg | 2.5 mg |
| Methyl Hydroxybenzoate | 10.0 mg | 120.0 mg | 1.32 mg | 13.2 mg | 6.6 mg |
| Ethyl Hydroxybenzoate | 10.0 mg | 120.0 mg | 0.66 mg | 6.6 mg | 3.3 mg |

Fig. 6 Topiramate suspension excipient limitations.

| | |
|---|---|
| Apparatus | USP II (Paddles) |
| Paddle speed | 58 rpm |
| Media | pH 1.2, 4.5 & 6.8 (as EP) |
| Sampling times | 10, 15, 20, 30, 45, 60 |
| Vessel Temperature | 37 ± 0.5 °C |
| Media volume | 500 ml |
| No. of Vessels | 12 per pH condition |
| Media replacement | None |
| Filters | Cannula filters & 0.45 μm nylon syringe |
| Detection / Analysis | HPLC-RID |

Fig. 7 Topiramate suspension dissolution test parameters.

ORAL TOPIRAMATE SUSPENSION FORMULATIONS WITH EXTENDED SHELF STABILITY AND ENHANCED BIOAVAILABILITY

CROSS REFERENCE TO RELATED APPLICATIONS

None.

FIELD OF THE INVENTION

The field of the invention generally relates to physicochemically stable pharmaceutical formulations suitable for oral administration comprising a therapeutically effective amount of topiramate in a pharmaceutically acceptable, aqueous, suspension-stabilizing vehicle.

BACKGROUND OF THE INVENTION

There exists a strong market demand for commercially available, shelf-stable oral liquid drug formulations that are bioequivalent to traditional solid dose drug formulations (e.g., tablets and capsules). Relative to solid dose formulations, oral liquid formulations (e.g., solutions, emulsions, suspensions, and syrups) are easier to swallow, demonstrate faster absorption kinetics, and are easier to titrate on a per patient basis. Other non-liquid drug formulation alternatives include easier to swallow tablets, capsules, sustained release formulations, transdermal patches, suppositories, lozenges, parenteral formulations, ocular formulations, inhalation formulations, sublingual tablets, topical formulations (e.g., creams, ointments, gels, pastes, lotions, powders), and/or easily reconstituted lyophilized formulations.

The pharmaceutical industry employs a variety of dosage formulations for orally administering medicinal agents to patients. Typical formulations for oral administration include liquid solutions, emulsions, or suspensions, as well as solid forms such as capsules or tablets (as used herein, the term "tablet" means any shaped and compressed solid dosage form, including caplets). Children, older persons, and many other persons have difficulty swallowing whole tablets and even capsules. Therefore, it is often desirable to provide the medicine either in liquid form or in a chewable solid form or an alternative solid form, e.g., small particle "sprinkles" which can be sprinkled onto soft food and swallowed intact with the food. While the administration of multiparticulate sprinkles is often indicated to improve the organoleptic properties of a drug, poor control over dose intake can impact bioavailability.

Physicochemically stable oral formulations capable of dose titration having extended shelf life and bioavailability comparable to approved solid dosage formulations would be much appreciated in the field of anticonvulsive therapy. Supportive of this claim, non-solid versions of the following anticonvulsants have been developed: clobazam, clonazepam, ethosuximide, lacosamide, levetiracetam, nitrazepam, oxcarbazepine, piracetam, phenobarbital, phenytoin, pregabalin, ralfinamide, and sodium valproate. Despite the ongoing need for non-fixed dose oral formulations of anticonvulsants, no liquid formulations (either liquid solutions or liquid suspensions) of topiramate have been commercially developed since topiramate was first approved in 1996. Of the five FDA approved branded drug products containing topiramate as an active ingredient (i.e., TOPAMAX®, TOPAMAX® SPRINKLE, TROKENDI® XR, QUDEXY® XR, and QSYMIA®) and twenty-nine FDA approved generic drug products containing topiramate as an active ingredient, all thirty-four formulations are solid dosage forms (e.g., capsules or tablets). Topiramate, a sulfamate substituted monosaccharide anticonvulsant, is the nonproprietary name for the compound 2,3:4,5-Bis-O-(1-methylethylidene)- -D-fructopyranose sulfamate (a.k.a., 2,3:4,5-Di-O-isopropylidene- -D-fructopyranose sulfamate), having the molecular formula $C_{12}H_{21}NO_8S$ and the chemical structure shown in FIG. 1.

Market demand for a broader range of intermediary topiramate doses has expanded since first approval in 1996. TOPAMAX® (topiramate) is currently sold in 25 mg, 50 mg, 100 mg, 200 mg, 300 mg and 400 mg solid tablet formulations as well as 15 mg and 25 mg solid capsule formulations. Additionally, TOPAMAX® SPRINKLE capsules comprise topiramate coated beads in a hard gelatin capsule available in 15 mg, 25 mg and 50 mg strengths intended to be manually opened and sprinkled onto soft food (e.g., for adjunctive adult therapy, pediatric patient populations and/or dose tapering). Other alternative oral formulations of topiramate include TROKENDI® XR extended release capsules available in 25 mg, 50 mg, 100 mg and 200 mg solid dose strengths. Similarly, QUDEXY® XR extended release capsules are available in 25 mg, 50 mg, 100 mg, 150 mg and 200 mg solid dose strengths of topiramate. Finally, QSYMIA® is a solid dose combination of phentermine hydrochloride and topiramate extended-release and is commercially available in 3.75 mg/23 mg, 7.5 mg/46 mg, 11.25 mg/69 mg, and 15 mg/92 mg strengths (phentermine mg/topiramate mg extended-release) indicated as an adjunct to a reduced-calorie diet and increased physical activity for chronic weight management in adults.

While many alternative oral formulations of topiramate have been developed (e.g., extended release solid, sprinkle capsule solid, wax based solid, nanoparticle solid, etc.), none are liquid formulations, either in solution or suspension.

SUMMARY

It is to be understood that both the foregoing general description of the embodiments and the following detailed description are exemplary, and thus do not restrict the scope of the embodiments.

In one aspect, the invention provides physicochemically stable, oral liquid suspension formulations of topiramate demonstrating consistent dosing, palatability, extended shelf stability and therapeutically relevant dosing and therapeutically relevant bioavailability. Such oral liquid suspension formulations of topiramate may demonstrate bioequivalence to previously approved solid dose drug formulations.

In another aspect, the invention provides a method for producing physicochemically stable, oral liquid suspension formulations of topiramate demonstrating consistent dosing, palatability, extended shelf stability and therapeutically relevant dosing and therapeutically relevant bioavailability.

In another aspect, the invention provides improved analytical methods for assaying complex drug formulations containing sulfamate-substituted monosaccharides such as topiramate.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1. Chemical structure of topiramate.
FIG. 2. Topiramate suspension compositions.
FIG. 3. Manufacture of topiramate suspension compositions
FIG. 4. Particle size distribution of topiramate suspension starting API.
FIG. 5. Viscosity, particle size, and dissolution parameters of topiramate suspensions.
FIG. 6. Topiramate suspension excipient limitations.
FIG. 7. Topiramate suspension dissolution test parameters.

DETAILED DESCRIPTION

The present application discloses the first example of an aqueous suspension of topiramate with extended physicochemical stability and therapeutic bioavailability equivalent to that of commercially approved solid dose formulations. Topiramate is a white crystalline powder with a third party reported solubility in room temperature water (25° C.) of 9.8 mg/mL, and is freely soluble in non-aqueous reagents such as acetone, chloroform, dimethylsulfoxide, and ethanol. See, Physician's Desk Reference, 56th ed., pp. 2590-2595 (2002). Topiramate may be produced according to the processes disclosed in U.S. Pat. Nos. 4,513,006 and 5,387,700, the entire contents of which are herein incorporated by reference. Topiramate is sold in the United States under the trade name TOPAMAX® (Ortho-McNeil Pharmaceutical, Inc., Raritan, N.J., U.S.A). TOPAMAX® has been approved for use as an antiepileptic agent as an adjuvant therapy for patients with partial onset seizures, or primary generalized tonic-clonic seizures. See generally, Physician's Desk Reference, 56th ed., 2590-2595 (2002); see also, U.S. Pat. No. 4,513,006.

In one representative and non-limiting embodiment, the invention may be seen to comprise a physicochemically stable aqueous composition including topiramate in suspension, wherein the pH of the composition is maintained in the range of about 4.5 to about 5.5. Preferably, the pH is maintained within the desired range using a citric-phosphate buffer pair and diluted hydrochloric acid buffer system. Preferably the buffer system is a citric acid monohydrate/disodium hydrogen phosphate dihydrate. Preferably, the disclosed aqueous composition including topiramate is physicochemically stable under extended cold-chain conditions for at least 24 months.

Definitions

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein and unless otherwise indicated, the term "topiramate" refers to 2,3:4,5-Bis-O-(1-methylethylidene)--D-fructopyranose sulfamate and isomers and mixtures of isomers thereof. In particular, while "topiramate" conventionally refers to the specific compound named 2,3:4,5-Bis-O-(1-methylethylidene)--D-fructopyranose sulfamate and represented by formula I, above, the term is used herein to refer to all enantiomerically and/or diastereomerically pure isomers of that specific compound, as well as mixtures of such isomers.

"Active agent" generally means a compound, macromolecule, drug, element, substance, or mixture that when administered to a patient, alone or in combination with another compound, macromolecule, element, substance, or mixture, confers, directly or indirectly, a physiological effect on the patient. When the active agent is a compound, then salts, solvates (including hydrates), esters, and prodrugs of the compound are contemplated herein. Furthermore, crystalline forms, non-crystalline forms, polymorphs and any pseudopolymorphs of the compound are also contemplated herein. "Active Agent" and "Active Pharmaceutical Ingredient" (API) are used interchangeably.

"D(0.9) value" refers to the threshold at which 90% of the particles in a sample are expected to be smaller as measured by particle size diameter. Unless noted otherwise, all D(0.9) values are in μm.

"Bioavailability" generally means the extent or rate at which an active agent is absorbed into a living system or is made available at the site of physiological activity. Bioavailability can be characterized by one or more pharmacokinetic parameters. "Pharmacokinetic parameters" describe the in vivo characteristics of an active agent (or surrogate marker for the active agent) over time, such as plasma concentration (C), $C_{max}$, $C_n$, $C_{24}$, $T_{max}$, and AUC. "$C_{max}$" is the measured concentration of the active agent in the plasma at the point of maximum concentration. "$C_n$" is the measured concentration of an active agent in the plasma at about n hours after administration. "$C_{24}$" is the measured concentration of an active agent in the plasma at about 24 hours after administration. The term "$T_{max}$" refers to the time at which the measured concentration of an active agent in the plasma is the highest after administration of the active agent. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t. $AUC_{0-INF}$ is the calculated area under the curve of plasma concentration versus time from time 0 to time infinity.

"Bioequivalence" generally means the absence of a significant difference in the rate and extent to which the active agent or surrogate marker for the active agent in pharmaceutical equivalents or pharmaceutical alternatives becomes available at the site of action when administered in an appropriately designed study.

"Pharmaceutically acceptable" generally means suitable for use in contact with the tissues of humans and animals without undue toxicity, irritation, allergic response, and the like, commensurate with a reasonable benefit/risk ratio, and effective for their intended use within the scope of sound medical judgment. By "pharmaceutically effective amount", it is generally meant the amount of an active agent that, when administered to a patient for treating a disease, is sufficient to effect such treatment for the disease. A pharmaceutically effective amount will vary depending on the active agent, the disease and its severity, and the age, weight, and other conditions of the patient to be treated.

"Shelf Stability" generally refers to the longest length of time in the labeling or approval documentation accompanying a commercially approved drug formulation. A product's "shelf stability" generally means the length of time you can expect a product to look and act as expected and to stay safe for use. In an embodiment, the labeling or approval documentation originates from the European Medicines Agency. In another embodiment, the labeling or approval documentation originates from the U.S. Food and Drug Agency (FDA). "Shelf Stability" can refer to either room temperature shelf conditions or cold-chain shelf conditions.

"Mutual compatibility" of the components means that the components do not separate in preparation and storage for up to the equivalent of two years under cold chain storage. Storage stability means that the materials do not lose their desirable properties during storage for the same period.

"Reference drug" or "Reference Listed Drug" (RLD) means an active pharmaceutical ingredient product as described in the U.S. Federal Food and Drug Administration's (FDA) Orange Book, Approved Drug Products with Therapeutic Equivalence Evaluations or the European Medicines Agency (EMEA) document "Note for Guidance on the Investigation of Bioavailability and Bioequivalence. In a preferred embodiment, the reference drug is the 200 mg dose of TOPAMAX™ approved by the U.S. FDA under NDA 020505.

The Problem of Solid, Fixed-Dose Drug Formulations

Patients who: (i) have difficulty in swallowing, (ii) feign ingestion, (iii) require non-standard commercial doses, (iv) are children or (v) are simply seeking more convenient and titratable alternatives to oral solid drug dosage forms, are often forced to seek out individually compounded liquid formulations using the active pharmaceutical ingredient (API) from crushed tablets. Such extemporaneously created suspensions are problematic, in part, because they were not designed to be physicochemically stable (e.g., the API crystallizes out of the compounded formulation and/or is chemically degraded). Such physiochemical instability invariably leads to highly variable API dosing with accompanying unpredictable therapeutic efficacy and side effects. Concerns over drug contamination (e.g., bacterial and/or fungal) and inaccurate dose strengths continue to be a problem for manually compounded drugs.

Dose titration is extremely difficult with fixed dose formulations (including the solid sprinkle capsule formulations of topiramate) and is particularly relevant for neuropsychiatric medications where optimal therapeutic efficacy is often determined on an individual patient basis that may vary on a daily basis. Often, optimal dosages of topiramate (e.g., 12 mg/ml, 61 mg/ml, etc.) are not available in standard solid dose formulations.

Solid dose drug formulations additionally pose adherence problems. Medication adherence to solid dose drug formulations is particularly problematic in (i) elderly and pediatric patient populations with swallowing difficulties, (ii) patients who feign drug ingestion (i.e., "cheeking") and (iii) patients sensitive to drug excipients normally found in solid oral dose formulations. Solid dose formulations also exhibit a lag time between ingestion and when therapeutic effects are observed.

The Solution of Liquid, Variable-Dose Drug Formulations

Liquid oral formulations (either pure liquid solutions or liquid suspensions) generally demonstrate faster pharmacodynamics (e.g., $T_{max}$) than their solid dose counterpart. This is particularly important for individuals actively experiencing a medical event (e.g., epilepsy, seizure, migraine, bipolar disorder, post traumatic stress disorder, etc.) who could be effectively treated with anticonvulsants such as topiramate. Other indications generally known to those skilled in the art are also amenable to the rapid therapeutic effects of an oral liquid suspension of topiramate. Thus, a clear need exists for alternative, non-solid oral formulations of topiramate with high bioavailability and extended physiochemical stability.

While commercial grade liquid oral drug formulations (e.g., both pure liquid solutions and liquid suspensions) demonstrating extended stability are generally far more physicochemically complex and difficult to manufacture than their solid dose counterparts, they benefit patients with more precise dosing options. Compared to pure liquid solution drug formulations, drug suspension formulations having commercially viable shelf lives are often far more physicochemically complex to manufacture. In part because of the unpredictability of suspension drug formulations, efforts to design drug suspensions are commonly initiated only after initial attempts to develop simpler liquid formulations have failed.

For drugs with low solubility and/or bioavailability at physiological pH and temperature, efforts to develop suspension formulations are often met with varying rates of success due to restrictive physiochemical parameters of the API and/or excipients. For example, while simply increasing the volume of diluent for low-solubility drugs may improve solubility, the large volume of diluent is often prohibitive from a patient perspective. Formulations in which the drug is solubilized using a co-solvent(s) often demonstrate unforeseeable precipitation and/or phase separation during long-term storage. Relative to room temperature stable drug formulations, drug formulations requiring cold-chain storage conditions often exhibit greater crystallization and/or precipitation anomalies. Therapeutically effective topiramate suspensions are particularly problematic since the API and subsequent oral suspension formulations must not only exhibit high bioavailability and bioequivalence, but also high physicochemical stability. Finally, as is the case for topiramate, forcing a relatively low solubility API (observed to be 8.3 mg/ml at 25 degrees Celsius in purified water) into aqueous solution at therapeutically relevant doses (10 mg/ml and higher) often requires conditions (e.g., pH>10) or solvents (e.g., acetone) well out of the range of acceptable oral tolerability.

Commercially successful drug products often have shelf stability longer than one year. While drug API in suspension is generally more chemically stable than fully soluble drug solutions, the chemical stability often comes at the expense of unpredictable physical instability. For example, drug suspensions tend to settle, phase separate, marble and/or agglomerate upon storage, particularly under cold-chain conditions. This unpredictability often leads to unacceptably high variations in dosing, consistency and/or palatability.

The failure of others to develop a commercially viable, therapeutically effective, shelf-stable (here, cold-chain) liquid oral topiramate formulation (i.e., those 10 mg/ml and higher), despite the commercial success of many other liquid oral anticonvulsant formulations (e.g., clobazam, clonazepam, ethosuximide, lacosamide, levetiracetam, nitrazepam, oxcarbazepine, piracetam, phenobarbital, phenytoin, pregabalin, rufinamide, and sodium valproate), suggests that while others may have contemplated the development of a liquid oral topiramate drug product, known physiochemical barriers likely precluded a reasonable expectation of success and/or demanded undue experimentation from one skilled in the art of drug reformulation. To this extent, we highlight the Clinical Pharmacology Review from NDA 20844 (S031, TOPAMAX®) as evidence of both a failure of others and long felt but unsolved commercial need to develop therapeutically effective, shelf-stable liquid oral topiramate formulations. In this clinical study, FDA suggested that only higher concentration oral topiramate formulations were therapeutically useful by concluding that a low dose 5 mg/ml oral pure liquid solution was not effective in treating children with partial onset of seizures.

Topiramate has been extensively investigated for a variety of therapeutic uses such as: an anti-obesity agent, a blood pressure lowering agent, and a mood stabilizer, including use as an antimonic, antidepressant, and for the treatment of post-traumatic stress disorder, migraines, cluster headaches, and neuropathic pain. See, e.g., U.S. Pat. Nos. 6,191,117; 6,201,010; 5,753,693; 5,998,380; 6,319,903; 5,935,933; and 5,760,007. However, the time it takes for topiramate to reach peak plasma levels (i.e., about two hours) can be too slow for its effective use in the treatment of some conditions, such as neuropathic pain. Moreover, the compound's relatively low aqueous solubility makes it difficult to formulate in a controlled release dosage form. Such dosage forms may be necessary for the effective treatment of conditions such as obesity, and which may allow a reduction in adverse effects associated with peak plasma levels of the drug. Novel topiramate formulations that are physicochemically stable and sufficiently bioavailable are needed to increase the safety and effectiveness of the compound in certain patient populations.

Known Therapeutic Uses of Topiramate

The exact mode of action of topiramate is unknown but is shown to effectively calm neuronal activity and reduce epileptic seizures. It is considered a broad-spectrum anti-epileptic drug (AED) because it works to prevent both partial onset and generalized seizures. The drug may also be useful for treating conditions including seizures, mood disorders, post traumatic stress syndrome (PTSD), bipolar disorder, mania (all forms, such as acute mania, severe treatment-refractory mania, bipolar mania, etc.), depression, personality disorders, bipolar mood instability, schizophrenia, psychosis, bipolar spectrum disorders, rapid-cycling bipolar disorders, and other disorders generally known to those skilled in the art. Topiramate is also useful for treating patients with mood disorders that have not been adequately controlled by other medications, such as lamotrigine and gabapentin, and for treating patients with bipolar mood disorders that have not responded to lithium and/or other mood-stabilizers.

Unexpected Physiochemical Challenges of Therapeutic Topiramate Liquid Products

Extensive reformulation efforts revealed the physiochemical nature of topiramate makes it extremely challenging to commercially develop stable, liquid oral formulations of topiramate. From a purely chemical perspective, topiramate is highly sensitive to heat (e.g., room temperature) and humidity (e.g., aqueous environment of liquid formulations). For example, abandoned U.S. Pat. App. No. 2006/0270611 discloses that topiramate is highly sensitive to hydrolysis in an aqueous medium and that any conventional aqueous oral solution would have a very limited shelf life. The chemical instability of topiramate is so well known, that pharmacists routinely monitor topiramate degradation by a change in physical appearance (e.g., tablet color changing from white to brown) and by an emergence of chemical breakdown byproducts (e.g., formation of sulfamate and sulphate ions and organic degradation compounds readily detected by HPLC). Mentioned earlier, the solubility of topiramate in water at 5 degrees Celsius and 25 degrees Celsius is 6.4 mg/ml and 8.3 mg/ml, respectively. Both of these values are generally considered to be sub-therapeutic with at least approximately 10 mg/ml being considered a therapeutic dose.

Topiramate Polymorphism

Therapeutically active pharmaceutical ingredients can present polymorphic forms by existing in different physical forms (e.g., as amorphous solid and/or varying crystalline forms). This phenomenon of identical chemical structure but disparate internal structure is generally referred to as chemical polymorphism. Polymorphism is a natural property resulting from the conditions under which a compound is manufactured or isolated. Polymorphs often have different physical properties, including solubility, and therefore different bioavailability. Another potential source of unpredictability in suspension drug formulation development lies in the existence of chemical polymorphism. Many pharmaceutical compounds can crystallize with more than one type of molecular packing structure and/or with more than one type of internal crystal lattice. Many pharmacologically active organic compounds can also crystallize such that a second, foreign molecule(s), especially solvent molecules, are regularly incorporated into the crystal structure of the principal pharmacologically active compound. This phenomenon is referred to as pseudopolymorphism and the resulting structures as pseudopolymorphs. When the second molecule is a solvent molecule, the pseudopolymorphs can be referred to as solvates. An important solid-state property of a pharmaceutical compound that can vary among polymorphs is its rate of dissolution in aqueous media (e.g., gastric fluid) and thus bioavailability. For a general review of polymorphs and the pharmaceutical applications of polymorphs see G. M. Wall, Pharm Manuf. 3, 33 (1986); J. K. Haleblian and W. McCrone, J. Pharm. Sci., 58, 911 (1969); and J. K. Haleblian, J. Pharm. Sci., 64, 1269 (1975), which is incorporated herein by reference.

Highlighting the uncertainty of polymorphism in the drug manufacturing process, occasionally there is an effect on long-term physiochemical stability if the most stable polymorph had not been selected for development in the first place. The practical effect of changing the polymorph is on the dissolution rate of the finished product and, potentially, an effect on bioavailability, and/or a change in the long-term stability profile. Highlighting the unpredictability of topiramate in a finished dosage formulation, topiramate was recently found to form a new polymorph in the presence of polyethylene glycol (PEG)—a common drug excipient (Yam, et al.).

U.S. Pat. No. 7,351,695 discloses various topiramate salts, polymorphs, solvates, hydrates, dehydrates, co-crystals, anhydrous, and amorphous forms. Co-crystals are crystalline materials composed of two or more different molecules, typically active pharmaceutical ingredient (API) and co-crystal formers ("coformers"), in the same crystal lattice. Co-crystals can be tailored to enhance drug product bioavailability and stability and to enhance the processability of APIs during drug product manufacture. Co-crystals are distinguished from salts because unlike salts, the components that co-exist in the co-crystal lattice with a defined stoichiometry interact non-ionically. In addition, co-crystals differ from polymorphs in that co-crystals are more similar to solvates, in that both contain more than one component in the lattice. From a physical chemistry and regulatory perspective, co-crystals can be viewed as a special case of solvates and hydrates, wherein the second component, the coformer, is not a solvent (including water), and is typically nonvolatile.

It is well known that screening for the presence of various polymorphs requires crystallization experiments from a diverse range of solvents. Moreover, for a specific solvent it is possible to obtain crystals with different symmetries depending on parameters such as pH and temperature (See Sena, et al.) While the raw source topiramate for the present invention produced a single melting endotherm on preliminary differential scanning calorimetry (DSC), topiramate is a sugar derivative, and thus does not have a sharp melting point. It is plausible that undetected trace salts, polymorphs, solvates, hydrates, dehydrates, co-crystals, anhydrous, and amorphous forms of topiramate played a role in the unexpected topiramate crystallization data.

To this end, investigations are planned to test whether trace polymorphism/crystallization plays a substantive role in the physical instability of topiramate both in solution and suspension. The characterization of new topiramate polymorphs is important because an understanding of the diverse solid-state forms can lead to better design and control of drug performance. Moreover, for a specific solvent it is possible to obtain topiramate crystals with different symmetries depending on parameters such as pH and temperature. While inconsistent drug particle size or drug impurities can affect the physical stability of drug suspensions, this did not appear to be responsible for the problematic crystal formation of the present invention as topiramate particle size was reproducibly consistent FIG. 4 and only trace impurities were observed.

Efforts toward developing shelf-stable, oral liquid formulations of topiramate bioequivalent to marketed products have largely been thwarted by significant physiochemical challenges including low solubility at physiologic pH, precipitation of drug product at therapeutically relevant API concentrations above 9.8 mg/ml, and elevated chemical instability at high pH (i.e., increasing solubility decreases stability) and/or room temperature (i.e., 25 degrees C.).

The following references outline current demand for alternative forms of topiramate pharmaceutical products. Significantly, none disclose liquid compositions containing topiramate. U.S. Pat. Nos. 9,492,380, 6,696,091 and U.S. Pat. App. Nos. U.S. 20140348931 and 20040156901 disclose chemical suspensions of topiramate, but only as an upstream chemical intermediary reagent for final solid dose products. U.S. Pat. No. 9,492,380 additionally discloses a rapidly dispersible, wax-based and taste-masked solid topiramate formulation. U.S. Pat. Nos. 7,351,695 and 6,699,840 disclose solid topiramate formulations containing polymorph, solvate, hydrate, dehydrate, co-crystal, anhydrous, and amorphous forms of topiramate. U.S. Pat. No. 7,390,505 discloses nanoparticle topiramate formulations. Solid dose extended release (ER) versions of topiramate are disclosed in U.S. Pat. No. 9,555,005 and U.S. Pat. App. Nos. 2018/0055778, 2003/0072802 and 2017/0368087. U.S. Pat. No. 6,559,293 discloses topiramate sodium trihydrate solid dosage formulations as well as an exhaustive prophetic wish list of other non-solid dosage forms of topiramate. Other prophetic examples of alternative formulations of topiramate containing drug products include: U.S. Pat. App. No. 2018/0177752 disclosing an oral drug suspension delivery device for drugs with short half-lives (e.g., levodopa), but additionally including non-enabled prophetic examples including anti-epileptics; U.S. Pat. App. No. 2018/0177733 disclosing rapidly dissolving vaginal tablets (enabled only for antifungals), but additionally including non-enabled prophetic examples including anti-epileptics; and U.S. Pat. App. No. 2018/0177756 disclosing a solid dose form comprising a therapeutically effective amount of A19-144 or A2-73 and a therapeutically effective amount of at least one anti-epilepsy drug. Importantly, prophetic examples (i.e., examples that are conceived and disclosed, but inoperative and/or not enabled) can provide evidence for both market demand and a failure of others.

Abandoned U.S. Pat. App. No. 2006/0270611 discloses a non-aqueous, dilutable, organic topiramate liquid pre-concentrate composition that teaches away from topiramate aqueous solutions as having very limited shelf life. U.S. Pat. App. No. 2007/0087976 teaches away from liquid suspensions by disclosing highly pure solid forms of topiramate having particle size less than 250 m as a means to render topiramate refractory to hygroscopic degradation. U.S. Pat. App. No. 2007/0077294 discloses taste-masked topiramate capsules capable of sprinkling on food. WO Pat. App. 2001/089445 seeks to avoid aqueous environment hydrolysis of topiramate by drying tablets to a residual free water content of from 0.4% to 1.4% before packing in blister packs. U.S. Pat. App. No. 2006/0121112 discloses a once-daily controlled-release pharmaceutical formulation containing therapeutic amounts of topiramate. U.S. Pat. App. No. 2009/0022794 discloses solid tablet dosage forms of topiramate and the problem of API degradation under humid conditions. U.S. Pat. App. No. 2007/003672 suggests making bi- or multiphasic tablets comprising in at least one of the phases a hygroscopic gum material and containing topiramate as the active ingredient in another phase than the gum material. U.S. Pat. No. 7,749,533 discloses a fast-melting pharmaceutical topiramate tablet comprises a porous, plastic substance, a water penetration enhancer and a binder. U.S. Pat. No. 5,738,875 discloses freeze-dried dosage forms as a means to avoid unpalatable drugs. U.S. Pat. No. 5,178,878 to Wehling et al. discloses a soft-compressed orodispersible dosage form. Effervescent dosage forms and quick release coatings of insoluble microparticles are described in U.S. Pat. Nos. 5,578,322 and 5,607,697. Freeze-dried foams and liquids are described in U.S. Pat. Nos. 4,642,903 and 5,631,023. Melt-spun dosage forms are described in U.S. Pat. Nos. 4,855,326, 5,380,473, 5,518,730 and 6,471,992. U.S. Pat. App. Nos. 2012/0207929 and 2003/0133975 disclose three-dimensionally printed rapidly dispersing dosage forms.

In addition to the problem of high instability, topiramate is known to have an extremely undesirable bitter taste. Taste-masked dosage forms for poorly tasting drugs have been developed. U.S. Pat. No. 6,767,557 suggests a reconstitutable powder containing drug encapsulated in a water insoluble enteric coating. U.S. Pat. Nos. 6,586,012 and 6,482,823 disclose a liquid formulation containing topiramate encapsulated in an acid soluble coating. U.S. Pat. App. No. 2018/0193270 discloses the use of exosomes to deliver topiramate. U.S. Pat. App. No. 2018/0193288 relates to methods and compositions including topiramate for the treatment or prevention of symptoms associated with post-traumatic stress disorder. U.S. Pat. App. No. 2012/0207836 suggests a film wafer formulation containing drug particles encapsulated in a cationic polyacrylate coating. U.S. Pat. App. No. 2012/0076858 suggests a rapidly dispersible formulation containing drug particles encapsulated in a cationic polyacrylate coating. U.S. Pat. App. No. 2012/0040001 suggests a rapidly dispersible compressed dosage form comprising drug, starch, binder and molding agent. U.S. Pat. App. No. 2011/0212171 discloses an orodispersible dosage form comprising topiramate particles coated with a water insoluble polymer. U.S. Pat. App. No. 2010/0285130 suggests a film formulation comprising a complex of drug and ion exchange resin coated with an ingestible polymer. U.S. Pat. App. Nos. 2010/0278901 and 2007/0092553 suggests a rapidly dispersible compressed dosage form comprising drug complexed to a resin. U.S. Pat. App. No. 2007/0154550 discloses an acrylate or ethyl cellulose coated powdered form of topiramate. U.S. Pat. App. No. 2006/0182796 discloses an acrylate and enteric polymer coated powder form of topiramate. U.S. Pat. App. No. 2007/0036732 describes multi-phasic topiramate tablets. U.S. Pat. App. No. 2006/0159758 discloses a taste-masked formulation containing an acrylate polymer in combination with another polymer. U.S. Pat. No. 6,106,861 discloses a rapidly disintegrable multiparticulate tablet that disintegrates in the mouth in less than 40 seconds and includes excipients selected from disintegrating agents, binding agents, and an active ingredient. The active ingredient is in the form of microcrystals coated with a taste masking coating that includes polymethacrylates and cellulose polymers such as hydroxypropyl-methyl cellulose, hydroxypropyl cellulose and cellulose acetophthalates. U.S. Pat. No. 6,136,347 describes flavor-masked pharmaceutical compositions that include microcapsules coated with water insoluble neutral methacrylic acid ester copolymers and triethylcitrate. PCT application WO 99/44581 discloses a process for taste masking of topiramate by coating the core with a taste masking coating mixture. The taste masking mixture includes cellulose acetate, cellulose acetate butyrate, methylcellulose, ethylcellulose or an Eudragit, and a disintegrant. U.S. Pat. App. No. 2006/0127479 discloses a taste-masked drug coated with an acrylate polymer. U.S. Pat. App. No. 2006/0039981 discloses a taste-masked drug coated with an acrylate polymer. US Pat. App. No. 2006/0088886 describes sulfamated topiramate analogs for use in immunodiagnostic assays.

The present invention discloses oral liquid suspension topiramate formulations from between about 10 mg/mL to about 20 mg/mL of topiramate. FIG. 2. More preferably, the concentrations of topiramate are approximately 10 mg/ml and 20 mg/ml. The most preferred compositions of the present invention contain 10 mg/ml and 20 mg/ml topiramate that remains physicochemically stable under cold-chain conditions (2-8 degrees C.) for at least 24 months. It will be apparent to those skilled in the art that such formulations can be co-administered with other therapeutic or prophylactic agents and/or medicaments that are not medically incompatible therewith. The method of manufacture of the cold-chain stable oral liquid topiramate suspension is detailed in FIG. 3.

The inventive oral composition has topiramate in a suspension formulation and can optionally include, for example, at least one pharmaceutical excipient selected from a buffer, an antioxidant, a chelating agent, a preservative, a tonicity adjuster, a cyclodextrin, a surfactant, a suspending agent, a wetting agent, a stabilizer, a flocculating agent, a sweetener, a flavoring, a colorant, a cosolvent, and other ingredients. Oral liquid formulations can contain taste-masking ingredients such as sweeteners (artificial and/or natural) and flavorings.

While drug suspensions can facilitate chemical stability, drug suspensions often exhibit detrimental physical instability due, in part, to unpredictable particle-particle interactions (e.g., caking and/or compaction of API and/or excipients) as well as complex particle-aqueous solution interactions. Settling and aggregation often result in drug formulations that are difficult to resuspend and/or are susceptible to phase separation leading to variable dose administration. While controlled flocculation has been shown to prevent caking (Sucker H., et al.), the commercial manufacture of stable suspensions by controlled flocculation is subject to limitations, since it is difficult to reproduce the optimum properties of suspension systems owing to the variability of the suspended solid and the stability of the excipients.

Ideal drug suspension formulations are pseudoplastic—demonstrating high viscosity at low shear rates (e.g., during shelf storage) and low viscosity at high shear rates (e.g., during shaking and pouring). Pseudoplastic suspending agents (as well as thixotropic agents) are desirable, since they recover slowly from the deformation that occurs through shearing (i.e., upon shaking, they remain fluid long enough to be poured).

The rate of sedimentation of a suspended phase can be estimated by Stoke's equation. While a useful starting point, this equation assumes that (i) all dispersed particles are of uniform shape and size and (ii) that the particles are sufficiently far apart so that the movement of one does not affect the neighboring particles. Moreover, the Stokes' equation does not consider all the additional variables affecting the stability of a suspension, including but not limited to, particle size and purity of both API and excipients, storage temperature, electrical charge of API and excipients, concentration of suspending agent, use of surfactants and wetting agents, antifoaming agents, co-solvents, pH adjusting buffer systems, antimicrobial preservatives and physiochemical compatibility with packaging materials (e.g., plastics, glass, rubber). While another source of physiochemical instability in suspension drug formulations lies in the source manufacturer of the API, this did not seem to affect the stability of topiramate oral suspension products. The particle size distribution (PSD) of topiramate starting API can be found in FIG. 4. Viscosity, particle size and dissolution (pH 4.5 at 45 minutes) of various topiramate suspension products can be found in FIG. 5.

The consistency of the physiochemical characteristics of the disclosed oral suspensions are typically influenced by a large number of variables, for example; the density of the internal and external phases; the ratio of the phase volumes; the viscosity of the external phase; and the dimensions, degree of aggregation, and shape of the particles. The variability of these parameters can cause difficulties during the development of the suspension, even after agitation at the time of use. In some cases, the difficulties lead to a nonhomogeneous distribution of the active agent.

Agglomeration is often an unpredictable physiochemical problem when developing drug suspension products. Agglomeration can modify the micrometric properties of pharmaceutical powders (e.g., flowability, packability and solubility) in unforeseen ways. Agglomeration can also influence phase segregation during processing and affect product bioavailability. Yari, et al. describes difficulties in understanding and reproducibly controlling process parameters governing agglomeration, the entire contents of which are herein incorporated by reference. In particular, Yari describes the uncertainties of how agglomerates form and evolve during the drug suspension manufacturing process using carbamazepine as a model API. Results show that agitation can influence the shape of the agglomerated particles in an unpredictable manner and that agglomeration of large crystals is often more difficult if they are elongated in shape. Smaller crystals on the other hand give rise to more spherical and larger agglomerates with smoother surface and denser structure.

The physical stability of drug suspensions can be controlled by the addition of flocculating agents to enhance particle dispersion and/or the addition of viscosity enhancers to reduce sedimentation rate in the flocculated suspension. While viscosity enhancers typically range from 0.5% to 5% of the final formulation, the ideal viscosity largely depends on a particle's unique chemistry and tendency to settle. Non-limiting examples of flocculating agents include, but are not limited to, electrolytes (e.g., KCL, NaCl), sulfates, citrates, phosphate salts, pH adjusting agents, alum, aluminium chlorohydrate, aluminium sulfate, calcium oxide, calcium hydroxide, iron (II) sulfate (ferrous sulfate), iron (III) chloride (ferric chloride), polyacrylamide, polyDADMAC, sodium aluminate, sodium silicate, chitosan, isinglass, *Moringa oleifera* seeds, gelatin, *Strychnos potatorum* seeds, guar gum, and alginates.

A commercially viable topiramate oral liquid formulation shall (i) be suitable for both adults and children (i.e., no alcohol content and preferably without propylene glycol), (ii) be sugar free, lactose free and gluten free, and (iii) have dosages of 10 mg/ml or greater.

After extensive failed efforts at room temperature, cold-chain storage was explored as a necessary component of any commercially successful topiramate product. Unfortunately, it was subsequently discovered that liquid solutions of topiramate display unpredictable physiochemical properties under cold-chain conditions (both pure liquid solutions and liquid suspensions). Paradoxically, a sub-therapeutic formulation of topiramate (i.e., 5 mg/ml) displayed an unexpected tendency to crystallize and precipitate out of solution relative to higher concentrations (e.g., 10 mg/ml and 20 mg/ml). A similarly unpredictable crystallization problem was observed for higher (e.g., 20 mg/ml) formulations at room temperature (i.e., 25 degrees C.) relative to lower concentration formulations. Moreover, early attempts at large-scale batch manufacturing demonstrated unexpected crystallization properties correlated with stirring parameters, minor temperature fluctuations, undetected crystal seeding and solution saturation at 5 degrees Celsius. We suspect that these unexpectedly challenging physiochemical properties of topiramate contributed to the failure of others to develop a stable, therapeutically relevant (10 mg/ml and higher) oral liquid formulation of topiramate bioequivalent to commercially approved solid dosage forms.

Solubility Failures

Topiramate is a white crystalline powder with a notoriously unpalatable bitter taste and maximum aqueous solubility in strongly alkaline solutions (i.e., approximately pH 9.5). As the reported solubility of topiramate in water (25 degrees C.) is 9.8 mg/ml, the feasibility of producing simple oral aqueous solutions at the 10 mg/ml and 20 mg/ml strengths would be expected to be extremely challenging. Surprisingly, routine observations recorded an even lower solubility of 8.3 mg/ml at 25 degrees Celsius and 6.4 mg/ml at 5 degrees Celsius. While the solubility of topiramate can be routinely enhanced with alkaline solutions containing sodium hydroxide or sodium phosphate having a pH above 9.0, such formulations are extremely unpalatable. Despite a perceived reasonable expectation of success of developing a low 5 mg/ml dose topiramate liquid formulation, chemical instability (i.e., hydrolysis) of topiramate in this formulation ensued after only two months under shelf storage conditions.

Customary attempts to reduce the chemical instability of topiramate by lowering storage temperature to 2-8° C. drastically increased the physical instability of topiramate (i.e., precipitation out of solution after two weeks). Routine attempts to alter pH also met with failure—decreasing the pH of a 5 mg/ml room temperature solution to below pH 8.5 rapidly degraded the topiramate, increasing the pH to above pH 8.5 rapidly degraded formulation preservatives.

Conventional buffers or buffer systems can be optionally added to drug formulations, for example, to maintain pH in a desired range, retain antimicrobial activity and/or enhance the solubility of the API. Suitable buffers are not chemically reactive with other ingredients and are present in amounts sufficient to provide the desired degree of pH buffering. In some embodiments, the buffer is selected to assist in maintaining a slightly basic pH of the liquid formulation and to balance electrical charges among API, suspending agents, and excipients allowing for optimal drug performance characteristics.

While the solubility of topiramate can be increased under highly alkaline conditions or with non-aqueous solvents such as acetone, ethanol, chloroform or DMSO, such solvents and pH levels are incompatible with oral administration. Moreover, at low pH, the topiramate degraded while at high pH, the preservatives degraded. Attempts to reverse titrate a more saturated alkaline topiramate solution back to an orally acceptable pH of 8.5 were also met with physical failure (i.e., topiramate precipitation) after two weeks.

Cold-Chain Failures

Cold-chain storage (e.g., 2-8 degrees C.) was selected in an attempt to counteract chemical heat sensitivity of topiramate. Unexpectedly, cold-chain solution products were not physically stable causing greater crystal formation and drug precipitation at lower topiramate concentrations (i.e., 5 mg/ml) than higher concentrations (e.g., 20 mg/ml). A similarly unpredictable crystallization problem was observed for higher (e.g., 20 mg/ml) formulations at room temperature (i.e., 25 degrees C.) relative to lower concentration formulations.

Successful Topiramate Oral Liquid Suspension Formulation Efforts

To overcome the above-described problems of developing a commercially viable liquid topiramate product with therapeutically relevant dosages at 10 mg/ml or greater, it was subsequently hypothesized that more physicochemically complex aqueous oral suspensions of topiramate may limit the physiochemical instability of the inventive composition while maintaining high bioavailability. Exemplary suspending agents include: acacia, tragacanth, xanthan gum, carbomer, alginates, carrageenan, locust bean gum, guar gum, gelatin, methylcellulose, hydroxymethylcellulose, hydroxypropylmethylcellulose, microcrystalline cellulose, powdered cellulose, hydroxy ethylcellulose, sodium carboxymethylcellulose (CMC), and synthetic hydrocolloids such as Carbopol™, Bentonite, Hectorite, Attapulgite, and Veegum K have also been used as suspending agents with mixed success.

While higher concentrations of topiramate (10 mg/ml and 20 mg/ml) demonstrated elevated physical stability, chemical stability was limited to 8 weeks at 25° C. Initial attempts to eliminate chemical instability by the use of cold chain storage were met with unexpected and confounding physical failures of crystal formation in the suspension product. For example, despite using the same batch of topiramate API, large topiramate crystals were unexpectedly seen only in the lower 5 mg/ml strength, but not in the higher 10 mg/ml and 20 mg/ml strengths. While the cause of topiramate crystal formation only in the 5 mg/ml strength is currently unknown, one possible explanation was attributed to temperature fluctuations upon storage and possible seeding of the crystals during lab analysis. Other explanations could include trace topiramate polymorph contaminants and/or solution saturation at lower topiramate concentrations only (e.g., 5 mg/ml). Current efforts are examining the role of manufacturing conditions on the formation of problematic topiramate crystals. Highlighting the difficulty of developing liquid suspensions of topiramate capable of retaining both physicochemical stability and therapeutically relevant bioavailability, only two formulations ultimately had commercially sufficient physicochemical shelf stability (i.e., greater than 24 months without crystal formation under cold chain conditions), acceptable bioavailability (i.e., equivalent to the approved solid dose TOPAMAX® formulation) and levels of excipients that were deemed safe for human exposure such that it could apply for regulatory marketing approval.

RID Analytical Method Development

During the development of a high bioavailability and shelf stable liquid topiramate formulations, a challenging step is choosing the appropriate analytical detector. The current trend in pharmaceutical API analysis is the development of faster HPLC and ultra liquid chromatography methods coupled with universal detection, mainly mass spectrometry or aerosol-based HPLC detectors. Some of the ideal characteristics of a universal HPLC detector include: high sensitivity, reproducibility, stability, wide linear range, compatibility with gradient elution, and non-destructive detection of the analyte and response unaffected by changes in the temperature/flow. For the simultaneous detection of multiple analytes, the detection choice and the HPLC method development is extremely challenging. Prior to this disclosure, no accurate methods existed for complex drug suspension formulations containing sulfamate substituted monosaccharide active pharmaceutical ingredients like topiramate. Existing drug substance assays were inaccurate due to the inherent imprecision of the evaporative light scattering detector (ELSD) method.

We suspect that a lack of readily accessible chromophoric moieties on the structure of topiramate contributes to the difficulty in successful development of topiramate containing liquid suspension drug products. Different analytical approaches to quantify topiramate by HPLC include: derivatization with fluorescent moieties and UV-absorbing moieties, conductivity detection, evaporative light scattering detection (ELSD), refractive index (RI) detection, chemiluminescent nitrogen detection (CLND) and MS detection. Some methods for the determination of topiramate by capillary electrophoresis (CE) and gas chromatography (GC) have also been published. Other than the presently described method, there is no unique chromatographic detection condition to analyze topiramate and its impurities in an aqueous environment containing drug excipients.

We additionally suspect that liquid oral solutions of topiramate have not been commercially developed because a commonly used analytical method (i.e., Index Detection a.k.a. "RID") cannot distinguish between topiramate and water-soluble excipients that co-elute with topiramate. Several other analytic methods have similarly proven difficult. For example, the capillary GC with flame ionization detection (FID) method failed due to the thermal instability of topiramate. Another failed approach was a reverse-phase HPLC method with light scattering detection, but the method was only suitable to analyze the drug substance and not low levels of degradation products. It has been suggested that topiramate likely has different degradation products in solution formulations compared with solid dosage forms. Moreover, very few non-chromatographic methods are reported in the literature to detect topiramate and correlated compounds. While HPLC is likely the most common separation technique, considerable effort is aimed at developing low-cost novel methods to analyze topiramate and its impurities in pharmaceutical formulations—particularly in non-solid dosage forms. Formulation development studies were further hindered by the fact that the drug substance assay results could not be read as accurate due to the inherent imprecision of the evaporative light scattering detector (ELSD) method. For this reason, an improved discriminatory dissolution method for the oral suspension was developed as a routine QC test in order to show batch consistency, product efficacy and to monitor the dissolution attributes of the product on stability.

Two issues were observed during the dissolution testing of the oral topiramate suspension: (i) the suspension produces very poor inter-vessel reproducibility with very large error values up until near dissolution completion and (ii) when comparing the reference tablet formulation with the suspensions very poor comparison is seen as the tablets tend to complete dissolution at a much faster rate. It was determined that both of these issues are caused by the physiochemical characteristics of the topiramate suspension vehicle and the release of the active ingredient from the suspension matrix. Once the suspension matrix is broken down, the topiramate becomes readily bioavailable. While unreliable data was seen for early time-points, successful discrimination can readily be observed using the proposed conditions at the 45 min time point. Changes in the physical nature of the product can also be detected with this novel testing approach.

Dissolution testing confirmed (i) that the inventive topiramate suspension demonstrates very poor inter-vessel reproducibility (e.g., not possible to perform traditional comparisons using the $F_2$ test (where % RSDs must be less than 10%) and (ii) comparison between the reference tablet formulation and the suspension formulation are poor. It was determined that these issues were related to the physical characteristics of the suspension vehicle and once the suspension matrix has degraded, the topiramate is readily available (i.e., BCS Class I or III).

Topiramate Flavoring and Taste Masking

Topiramate has a very bitter taste that lingers in the mouth for a considerable amount of time afterwards. A major requirement of any such solid form is that it must be palatable, since an unpalatable formulation greatly increases the risk of a patient neglecting to take a medication. Initial taste assessment of all topiramate formulations found that topiramate had a very bitter taste. Flavor masking experiments were carried out using lab batches and assessed against the method for suitability and organoleptic taste masking. A batch of topiramate 20 mg/ml oral suspension was used in a flavoring trial. Several flavors were taste tested and in line with the pediatric formulation development guideline a flavor was chosen that did not contain alcohol or propylene glycol. The flavor chosen after the assessment was blackcurrant. This flavor is propylene glycol free and does not contain alcohol. The blackcurrant flavor is adsorbed onto a maltodextrin derivative which may be either moderately sweet to almost flavorless. Sucralose was chosen as a non-cariogenic sweetener and the preferred level of sweetness that suitably masked the bitterness of the drug was at 0.2% w/v.

Preservatives

Topiramate oral suspensions disclosed herein are to be supplied as a multidose preparation and therefore are at risk of microbial growth. Alcohol, benzoates, parabens, phenols, quaternary ammonium compounds (i.e., quats), sorbic acid, salts and other substances generally known to one of skill in the art have all been employed as preservative agents for suspension formulations. A combination of methyl hydroxybenzoate and ethyl hydroxybenzoate was selected as a preservation system since they have synergistic antimicrobial activity in the pH range of the inventive composition of matter. Propylene Glycol was not required as sodium salts were used to enable dissolution of the parabens in the final formulation. While the sodium salts of methyl hydroxybenzoate and ethyl hydroxybenzoate are highly water soluble, they are also hygroscopic and can contain up to 5% moisture. Care was taken to adjust the amount of the sodium parabens to account for both the variable water content and the sodium salt, thus ensuring that the product contains the correct amounts of paraben free acids (the active part of the molecule effective against microbes).

Thickening Agents

In order to suspend the topiramate drug substance, it was necessary to add a suitable suspending agent to the formulation. It was found that xanthan was capable of suspending the topiramate at an optimized level of 0.5% w/v. The level of suspending agent was suitable to ensure minimal sedimentation was seen during storage over shelf life. Any sedimentation was easily re-suspended when shaken.

Anti-Foaming Agents

The manufacturing process for the topiramate suspension drug product required use of a mixer to hydrate the suspending agent and ensure efficient dispersion of the active. This in turn aerates the product and produces excessive foam on the surface of the product. It was determined that the use of an antifoaming agent was necessary. A variety of antifoaming agents exist, including: oil based defoamers (e.g., ethylene bis stearamide (EBS), paraffin waxes, ester waxes and fatty alcohol waxes), powder defoamers (e.g., silica), water based defoamers (e.g., mineral oil, vegetable oil, long chain fatty alcohol, fatty acid soaps or esters), silicone based defoamers (e.g., Polydimethylsiloxane), EO/PO based defoamers (e.g., polyethylene glycol and polypropylene glycol copolymers) and alkyl polyacrylates. Simethicone emulsion was ultimately found to be compatible with the API (and excipients) and able to ensure a suspension product that did not separate for at least a twenty-four month shelf life under cold chain conditions.

Surfactants

It is preferable that solid topiramate particles distribute homogeneously in the suspension to ensure accurate and reproducible dosing. Unfortunately, solid particles of suspension are not easily wetted by water due to their hydrophobic nature. Some wetting agent, acting as surfactants, accomplish this by reducing the interfacial tension between the solid particle and the liquid medium. Surfactants have disadvantages in that (i) they have foaming tendencies, (ii) are bitter in taste, and (ii) interact with preservatives (e.g., methyl paraben) and reduce antimicrobial activity. Surfactants can generally include: polymeric surfactants, anionic surfactants cationic surfactants, non-ionic surfactants and amphoteric surfactants. Non-limiting specific examples can include sodium lauryl sulfate, glyceryl laurate, polyoxamers and benzalkonium chloride. Surprisingly, the disclosed invention did not require surfactants to ensure uniform particle distribution and consistent API dosing.

Excipients

Pharmaceutical excipients are pharmaceutically acceptable ingredients that are essential constituents of virtually all pharmaceutical drug products. The inventive topiramate suspensions may comprise at least one additional component selected from the group consisting of excipients, surface active agents, dispersing agents, sweetening agents, flavoring agents, coloring agents, preservatives, oily vehicles, solvents, suspending agents, dispersing agents, wetting agents, emulsifying agents, demulcents, buffers, salts, spreading agents, antioxidants, antibiotics, antifungal agents and stabilizing agents.

Non-limiting examples of excipients individually suspected of causing adverse events include: acacia, acesulfame, acesulfame potassium, acetic acid, acetone, acetyltributyl citrate, alcohol, alginic acid, alpha-tocopherol, aluminum chloride, aluminum chlorohydrex propylene glycol, aluminum hydroxide, aluminum lake dyes, aluminum oxide, aluminum silicate, aluminum stearate, aluminum sulfate, amide resin, aminobenzoate sodium, ammonia ammonio methacrylate copolymer, ammonio methacrylate copolymer type A, ammonio methacrylate copolymer type B, ammonio methacrylate copolymers, ammonium chloride, ammonium hydroxide, ammonium laureth-5 sulfate, ammonium phosphate dibasic, artificial flavor, artificial grape flavor, artificial mint flavor, ascorbic acid, ascorbyl palmitate, aspartame, aspartame powder, banana barium sulfate, benzalkonium chloride, benzoic acid, benzyl alcohol, betadex black currant, black currant flavor, black ink black pigment, blackberry, blue dye, butyl alcohol, butylated hydroxyanisole, butylated hydroxytoluene butylparaben, calcium, calcium carbonate, calcium phosphate, calcium phosphate dibasic anhydrous, calcium phosphate dihydrate dibasic, calcium silicate, calcium stearate, calcium sulfate, calcium sulfate anhydrous, calcium sulfate dehydrate, candelilla wax, candelilla wax powder, carbomer, carbomer 934, carbomer 934p, carbomer homopolymer type A, carbomer homopolymer type B, carbomer homopolymer type C, carboxymethylcellulose, carboxymethylcellulose calcium, carboxymethylcellulose sodium, carmine, carnauba wax, carrageenan, castor oil, castor wax, cellacefate, cellulose, cellulose acetate, cellulose compounds, cellulose powdered, cellulosic polymers, cetostearyl alcohol, cetyl alcohol, cetylpyridinium chloride, cherry, citric acid, citric acid anhydrous, citric acid monohydrate, cochineal, coconut oil colophony colorants, coloring agent, compressible sucrose, compressible sugar, confectioners sugar, copovidone, corn, corn oil, corn starch, corn syrup, corn syrup solids, corn-derived proteins, cottonseed oil, cranberry, croscarmellose sodium, croscarmellose sodium type A, crospovidone, cysteine hydrochloride, D&C Blue No. 1, D&C Green No. 5, D&C Red No. 21, D&C Red No. 22, D&C Red No. 27, D&C Red No. 27 Aluminum Lake, D&C Red No. 27 Lake, D&C Red No. 28, D&C Red No. 28 Aluminum Lake, D&C Red No. 30, D&C Red No. 30 Aluminum Lake, D&C Red No. 33, D&C Red No. 40, D&C Red No. 6, D&C Red No. 6 Lake, D&C Red No. 7, D&C Red No. 7 Calcium Lake, D&C Yellow No. 10, D&C Yellow No. 10 Aluminium Lake, D&C Yellow No. 10 Lake, D&C Yellow No. 5, D&C Yellow No. 6, dehydrated alcohol, dextrates, dextrose, dextrose monohydrate, dibasic calcium phosphate, dibutyl phthalate, dibutyl sebacate, dicalcium phosphate, diethyl phthalate, dihydroxyaluminum sodium carbonate, dimethicone, dimethylaminoethyl methacrylate-butyl methacrylate-methyl methacrylate copolymer, dimethylpolysiloxane docusate sodium, dyes, edetate calcium disodium, edetate disodium edible black ink, egg lecithin, erythrosine, erythrosine sodium, ethanolamine, ethyl acrylate-methyl methacrylate copolymer, ethyl alcohol, ethyl butyrate, ethyl isovalerate, ethylcellulose ethylcellulose (10 mPa·s), ethylcellulose (100 mPa·s), ethylcellulose (20 mPa·s), ethylcellulose (7 mPa·s), ethylcellulose, ethylene glycol monoethyl ether, ethylvanillin, eudragit FD&C Blue No. 1, FD&C Blue No. 1 Aluminium Lake, FD&C Blue No. 1 Lake, FD&C Blue No. 2, FD&C Blue No. 2 Aluminium Lake, FD&C Blue No. 2 Lake, FD&C Green No. 3, FD&C Green No. 3 Aluminum Lake, FD&C Red No. 3, FD&C Red No. 4, FD&C Red No. 40, FD&C Red No. 40 Aluminium Lake, FD&C Red No. 40 Lake, FD&C Yellow No. 10, FD&C Yellow No. 10 Aluminum Lake, FD&C Yellow No. 10 Lake, FD&C Yellow No. 5, FD&C Yellow No. 5 Aluminum Lake, FD&C Yellow No. 5 Lake, FD&C Yellow No. 6, FD&C Yellow No. 6 Aluminum Lake, FD&C Yellow No. 6 Lake, ferric oxide, ferric oxide black, ferric oxide brown, ferric oxide orange, ferric oxide red, ferric oxide yellow, ferric oxides, ferrosoferric oxide, ferrous, ferrous oxide, flavor, flavors, fragrances, fumaric acid, gelatin, glucosamine, glucosamine hydrochloride, glutamic acid hydrochloride, glycerin, glycerol, glycerol monooleate, glycerol monostearate, glyceryl behenate, glyceryl distearate, glyceryl monooleate, glyceryl monostearate, glyceryl triacetate, glycine, glycolate, glycyrrhizin ammoniated, guar gum, hard gelatin capsule, hard paraffin, hydrochloric acid, hydrochloric acid, hydrogen peroxide, hydrogenated castor oil, hydrogenated cottonseed oil, hydrogenated soy oil, hydrogenated soybean oil, hydrogenated vegetable oil, hydroxyethyl cellulose, hydroxypropyl cellulose, hydroxypropyl methylcellulose, hydroxypropyl methylcellulose phthalate, hypromellose, hypromellose 2208, hypromellose 2208 (100 mPa·s), hypromellose 2208 (100000 mPa·s), hypromellose 2208 (15000 mPa·s), hypromellose 2208 (3 mPa·s), hypromellose 2208 (4000 mPa·s), hypromellose 2910, hypromellose 2910 (15 mPa·s), hypromellose 2910 (15000 mPa·s), hypromellose 2910 (3 mPa·s), hypromellose 2910 (5 mPa·s), hypromellose 2910 (50 mPa·s), hypromellose 2910 (6 mPa·s), hypromellose 2910 3 cp, hypromellose 2910 50 cp, hypromellose 2910 Sep, hypromellose 2910 6 cp, hypromellose 3 cp, hypromellose Sep, hypromellose 6 cp, hypromellose phthalate, hypromelloses, indigotindisulfonate sodium, iron, isobutylparaben, isopropyl, isopropyl alcohol, lactitol, lactitol monohydrate, lactose, lactose anhydrous, lactose hydrous, lactose monohydrate, lecithin, lemon oil, leucine, light mineral oil, low substituted hydroxypropyl cellulose, magnesium, magnesium aluminum silicate, magnesium carbonate, magnesium hydroxide, magnesium oxide, magnesium oxide heavy, magnesium silicate, magnesium stearate, magnesium trisilicate, maleic acid, malic acid, maltodextrin, mannitol, medium-chain triglycerides, meglumine, menthol, methacrylic acid, methacrylic acid-ethyl acrylate copolymer (1:1) type a, methacrylic acid-methyl methacrylate copolymer (1:1), methacrylic acid-methyl methacrylate copolymer (1:2), methacrylic acid copolymer, methacrylic acid copolymer type B, methanol, methyl alcohol, methyl cinnamate, methyl methacrylate, methylcellulose, methylcellulose (100 mPa·s), methylcellulose (15 mPa·s), methylcellulose (400 mPa·s), methylene chloride, methylparaben, methylparaben sodium, microcrystalline cellulose, microcrystalline wax, mineral oil, mint, mint cream flavor, mint menthol, modified corn starch, monosodium citrate, natural and artificial orange flavor, natural flavor, natural mint flavor, natural peppermint flavor, natural resin, nonoxynol-100, oleic acid, olive oil, opacode black, orange cream flavor, orange juice, orange oil, orange-pineapple flavor, other ingredients known to those skilled in the art, palm kernel oil, paraffin, partially hydrogenated soybean and palm oils, peanut oil, peppermint, peppermint flavor, peppermint oil, pharmaceutical glaze, phenylalanine, phosphoric acid, piperazine, polacrilin potassium, polacrilin sodium, poloxamer, poloxamer 188, poloxamer 407, polyacrylate dispersion 30%, polycarbophil, polydextrose, polyethylene glycol, polyethylene glycol 1450, polyethylene glycol 300, polyethylene glycol 3000, polyethylene glycol 3350, polyethylene glycol 400, polyethylene glycol 4000, polyethylene glycol 600 polyethylene glycol 6000, polyethylene glycol 800, polyethylene glycol 8000, polygalacturonic acid, polyplasdone xl, polysorbate, polysorbate 20, polysorbate 80, polyvinyl acetate, polyvinyl alcohol, polyvinylpyrrolidone, potassium, potassium bicarbonate, potassium bitartrate, potassium carbonate, potassium carbonate anhydrous, potassium chloride, potassium gluconate, potassium hydroxide, potassium sorbate, potato starch, povidone, povidone k12, povidone k25, povidone k29/32, povidone k30, povidone k90, precipitated calcium carbonate, pregelatinized corn starch, pregelatinized starch, propyl gallate, propylene glycol, propylene glycol alginate, propylparaben, propylparaben sodium, raspberry, raw sugar, riboflavin, rice starch, saccharin, saccharin sodium, sd-45 alcohol, sda-3a alcohol, sesame oil, shellac, silicified microcrystalline cellulose, silicon dioxide, silicon dioxide colloidal, silicone, simethicone, simethicone emulsion, sodium, sodium alginate, sodium ascorbate, sodium benzoate, sodium bicarbonate, sodium carbonate, sodium carbonate monohydrate, sodium caseinate, sodium chloride, sodium citrate, sodium citrate dehydrate, sodium glycolate, sodium hydroxide, sodium laureth sulfate, sodium lauryl sulfate, sodium metabisulfite, sodium monolaurate, sodium phosphate, sodium phosphate dibasic, sodium propionate, sodium starch glycolate, sodium starch glycolate type A potato, sodium stearate, sodium stearyl, sodium thioglycolate, sodium tripolyphosphate, sorbic acid, sorbitan, sorbitan monolaurate, sorbitan monooleate, sorbitol, sorbitol special, soya lecithin, soybean oil, spearmint, starch, stearic acid, stearyl alcohol, strawberry, strawberry guarana flavor, strong ammonia solution, succinic acid, sucralose, sucrose, sucrose stearate, sugar 6x powder, sugar spheres, sunflower oil, synthetic ferric oxide, synthetic ferric oxide black, synthetic ferric oxide red, synthetic ferric oxide yellow, synthetic ferric oxides, tapioca starch, tartaric acid, tartrazine, taurine, TIMERx-N, titanium dioxide, titanium oxide, tragacanth, triacetin, tribehenin, tricalcium phosphate, triethyl citrate, trimyristin, trisodium citrate anhydrous, trisodium citrate dehydrate, tromethamine, tropical blend flavor, vanilla, vanilla flavor, vanillin, vitamin e, water, wax, wheat starch, white wax, xanthan gum, xylitol, yellow wax, zinc gluconate, zinc stearate.

While drug excipients often improve physiochemical stability in solid dosage formulations, the presence of excipients in suspension formulations is another source of both chemical and physical variability that can impact final product specifications (e.g., bioavailability and bioequivalence). Moreover, many excipients are known to be toxic above certain individual thresholds or in combination with other excipients and/or APIs. Persons of ordinary skill in the art would understand that both the U.S. Food and Drug Administration (FDA), the World Health Organization (WHO) and other related entities list maximum recommended daily intake limits of drug excipients to avoid excipient mediated toxicities. The World Health Organization (WHO) has specified a maximum daily allowance limit for the following excipients present within the inventive formulation FIG. 6. Only those excipients for which WHO limits are specified are disclosed. Formulation excipients not listed in the above table are known to be generally safe to use and do not have any WHO limits.

Buffering Agents

Buffering systems affect the physical stability and appearance of drug formulations. A variety of buffering systems are known in the art and include various forms of acetates (especially acetic acid and sodium acetate), citrates (especially citric acid and sodium citrate), and phosphates (especially sodium phosphate and disodium phosphate). During the development process, addition of simethicone to the formulation resulted in an unacceptable marbled and thin suspension at higher API loading (100 mg/5 ml). Subsequent addition of a proprietary citrate:phosphate buffer system was shown to improve the appearance and physical stability of the inventive formulations across all product API strengths.

Drug Product Scale-Up

As part of the process validation (PV) exercise, the 10 mg/ml and 20 mg/ml finished product were scaled up in the laboratory to 10 liters and placed on long term accelerated stability at 5° C., 25° C., 30° C. and 40° C. The product was then packaged into 180 mL (150 ml fill) amber Type III glass bottles.

Bioequivalence

Process validation batches were manufactured using the final production equipment and facility to cGMP and compared to a reference product (TOPAMAX® 200 mg Tablets) using dissolution (paddles 58 RPM) at three pH levels (i.e., 1.2, 4.5 and 6.8). FIG. 7. Dissolution completion (>85%) was achieved under all tests after 45 min, but the overall profile of the oral suspension product did not qualitatively compare well under routine test conditions. Despite the poor dissolution testing comparison, a clinical trial surprisingly revealed the in vivo bioequivalence of the topiramate suspension to the reference product. A study conducted in health volunteers demonstrated the 90% confidence intervals of the test/reference ratio for AUC and C max values for topiramate suspension lie within the acceptable limits of 80.00% to 125.00%, in line with the "Guideline on the Investigation of Bioequivalence (CPMP/EWP/QWP/1401/98 Rev 1/Corr**"). Thus, data support the claim that the disclosed 10 mg/ml and 20 mg/ml oral liquid topiramate suspension products are bioequivalent to the reference product TOPAMAX® 200 mg tablets (Janssen Cilag, Ltd.).

Bottle, Closure, Pack Size & Compatibility

Amber Type III glass complies with European Pharmacopoeia quality and is suitable for liquid preparations for oral use. The closure consists of HDPE, EPE wadded, tamper evident, child resistant closure. Topiramate oral suspensions will be available in two pack sizes. A fill volume of 150 ml into a 180 ml and 280 ml into a 300 ml amber type III glass bottles. The product may optionally be supplied with a 3 ml syringe (for the 10 mg/ml strength) or a 5 ml syringe (for the 20 mg/ml strength). The graduation is printed on the measuring device in such a manner to allow accurate and precise dosing. If low doses of topiramate are required, the 10 mg/ml strength product is most suitable. If high doses are required, the 20 mg/ml strength product is the most suitable. This product is a suspension and cannot be diluted prior to use.

Drug Formulation Effort Summary

Despite market demand, there are currently no commercially available shelf-stable liquid formulations of topiramate (either pure liquids or suspensions). We suspect this is a result of the inherently problematic physiochemical nature of topiramate in non-solid dose oral formulations. While several steps of formulation development were arguably routine (e.g., taste masking), significant novel and non-obvious efforts were made to overcome inherent problems of topiramate including (i) chemical instability of API at room temperature (e.g., due to pH), (ii) physical instability at cold chain temperatures (e.g., precipitation of API), (iii) unexpected API crystal formation (e.g., possibly due to trace polymorphs), and finally (iv) a lack of reliable analytical methods for assaying sulfamate substituted monosaccharides (i.e., topiramate) in a complex milieu of drug excipients.

Despite a clear market need for alternative, bioequivalent oral liquid formulations of anticonvulsants, no commercially available liquid formulations of topiramate exist. The invention is a novel and nonobvious improvement over all previously described solid oral topiramate formulations, at least in part, because the inventive drug formulation allows for uniform and consistent delivery of drug substance to a patient in need thereof throughout the entire extended cold chain shelf life of the product.

The foregoing describes the invention, including preferred forms thereof, alterations or modifications as would be understood to a person skilled in this particular art are intended to be included within the scope of the invention as claimed. In describing embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. The described embodiments of the invention may be modified or varied, and elements added or omitted, without departing from the invention, as appreciated by those skilled in the art in light of the disclosed teachings. Each reference cited herein is incorporated by reference as if each were individually incorporated by reference.

Literature

1. Diniz M. Sena Jr., Paulo T. C. Freire, Josue M. Filho, Francisco E. A. Melo, Fenelon M. Pontes, Elson Longo, Odair P. Ferreirae and Oswaldo L. Alvese. Vibrational and Thermal Properties of Crystalline Topiramate.
2. The USP Method for Topiramate Assay using UPLC and Refractive Index Detection. http://www.waters.com/webassets/cms/library/docs/720004643en.pdf
3. Eduardo Costa Pinto, Maressa Danielli Dolzan, Lucio Mendes Cabral, Daniel W. Armstrong, and Valeria Pereira de Sousa. Topiramate: A Review of Analytical Approaches for the Drug Substance, Its Impurities and Pharmaceutical Formulations.
4. Sucker H., Fuchs P., Speiser P., Pharmazeutische Technologie, 5th Edition 1991, Georg Thieme Verlag, Stuttgart, p. 423.
5. Physician's Desk Reference, 56th ed., 2590-2595 (2002).
6. G. M. Wall, "Pharmaceutical Applications of Drug Crystal Studies," Pharmaceutical Manufacturing, vol. 3, No. 2, February 1986, pp. 33-42
7. J. Haleblian and W. McCrone, "Pharmaceutical Applications of Polymorphism," Journal of Pharmaceutical Sciences, vol. 58, No. 8, August 1969, pp. 911-929 J. Pharm. Sci., 58,911 (1969).
8. J. K. Haleblian, "Characterization of Habits and Crystalline Modification of Solids and Their Pharmaceutical Applications," Journal of Pharmaceutical Sciences, vol. 64, No. 8, August 1975, pp. 1269-1288.

The invention claimed is:

1. A pharmaceutical composition comprising a pharmaceutically effective amount of topiramate particles dispersed in suspension, wherein the composition is suitable for oral delivery, characterised in that approximately ninety percent of topiramate starting material has a maximum particle diameter between 7 µm and 13 µm, wherein the topiramate concentration is 10 mg/ml or 20 mg/ml, wherein the D(0.9) value of the 20 mg/ml composition is approximately 26 µm to 35 µm and viscosity approximately 1177 to 2155 cP, wherein the D(0.9) value of the 10 mg/ml composition is approximately 21 µm to 36 µm and viscosity approximately 1175 to 2000 cP.

2. The composition of claim 1, wherein the pH is between about 4.5 and 5.5, is storage stable, and has a viscosity of approximately 1150-2200 cP.

3. The composition of claim 1, wherein the composition is bioequivalent to commercially approved solid dosage formulations of topiramate.

4. The composition of claim 1, wherein the composition is at least 24-month storage stable at 2 to 8 degrees centigrade.

5. A method of treating a patient in need thereof with a pharmaceutically appropriate dose of the pharmaceutical composition of claim 1.

\* \* \* \* \*